(12) United States Patent
Gehin

(10) Patent No.: US 8,222,496 B2
(45) Date of Patent: Jul. 17, 2012

(54) GARDEN BEAN CULTIVAR H37113

(75) Inventor: Robert J. Gehin, Belleville, WI (US)

(73) Assignee: Harris Moran Seed Company, Modesto, CA (US)

( * ) Notice: Subject to any disclaimer, the term of this patent is extended or adjusted under 35 U.S.C. 154(b) by 244 days.

(21) Appl. No.: 12/718,744

(22) Filed: Mar. 5, 2010

(65) Prior Publication Data

US 2011/0219471 A1 Sep. 8, 2011

(51) Int. Cl.
*A01H 4/00* (2006.01)
*A01H 5/00* (2006.01)
*A01H 5/10* (2006.01)
*C12N 15/82* (2006.01)

(52) U.S. Cl. ........ 800/313; 435/410; 800/260; 800/278; 800/279; 800/298; 800/300; 800/301; 800/302

(58) Field of Classification Search ........................ None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,850,009 A | 12/1998 | Kevern | |
| 5,968,830 A | 10/1999 | Dan et al. | |
| 6,201,170 B1 | 3/2001 | Magnuson | |
| 6,211,444 B1 | 4/2001 | Gehin | |
| 6,452,073 B1 | 9/2002 | Magnuson | |
| 6,835,876 B2 | 12/2004 | Magnuson | |
| 6,911,586 B2 | 6/2005 | Gehin | |
| 6,924,419 B2 | 8/2005 | Magnuson | |
| 7,385,119 B2 | 6/2008 | Gehin | |
| 7,439,423 B2 | 10/2008 | Gehin | |
| 7,473,824 B2 | 1/2009 | Gehin | |
| 7,511,197 B1 | 3/2009 | Gehin | |
| 7,514,608 B1 | 4/2009 | Gehin | |
| 7,645,924 B2 * | 1/2010 | Gehin | 800/313 |
| 2011/0023171 A1 | 1/2011 | Gehin | |
| 2011/0023172 A1 | 1/2011 | Gehin | |
| 2011/0023173 A1 | 1/2011 | Gehin | |
| 2011/0167511 A1 | 7/2011 | Gehin | |
| 2011/0191891 A1 | 8/2011 | Gehin | |
| 2011/0219467 A1 | 9/2011 | Gehin | |
| 2011/0219468 A1 | 9/2011 | Gehin | |
| 2011/0219469 A1 | 9/2011 | Gehin | |
| 2011/0219470 A1 | 9/2011 | Gehin | |

OTHER PUBLICATIONS

U.S. Appl. No. 12/510,070, Gehin, R. J.
U.S. Appl. No. 12/510,097, Gehin, R. J.
U.S. Appl. No. 12/510,119, Gehin, R. J.
U.S. Appl. No. 12/651,916, Gehin, R. J.
U.S. Appl. No. 12/697,554, Gehin, R. J.
Allard, 1960. Principle of Plant Breeding. John Wiley & Sons, Inc. p. 50-60.
Bassett, et al., 1975. The Role of Leaf Shape in the Inheritance of Heading in Lettuce. J. Amer. Soc. Hort. Sci. 100(2):104-105.
Bassett, et al., 1999. Allelism Found between Two Common Bean Genes, Hilum Ring Color (D) and Partly Colored Seedcoat Pattern (Z), formely Assumed to be Independent. J. Amer. Hort. Sci. 124 (6): 649-653.
Darnell, et al., 1990. DNA Replication, Repair and Recombination. *In* Molecular Cell Biology, 2nd edition, W.H. Freeman and Co., p. 478-487.
Eshed, et al., 1996. Less-Than-Additive Epistatic Interactions of Quatitative Trait Loci in Tomato. Genetics 143:1807-1817.
Kraft, et al., 2000. Linkage Desequilibrium and Fingerprinting in Sugar Beet. Theor. Appl. Genet. 101:323-326.
Poehlman, J.M. and Sleeper, D.A., Methods in Plant Breeding. *In* Breeding Field Crops, 5th ed. (2006), Iowa State University Press, pp. 171-183.
U.S. Appl. No. 12/718,695, Gehin, R. J.
U.S. Appl. No. 12/718,730, Gehin, R. J.
U.S. Appl. No. 12/718,715, Gehin, R. J.
U.S. Appl. No. 12/718,667, Gehin, R. J.

* cited by examiner

*Primary Examiner* — Stuart F. Baum
(74) *Attorney, Agent, or Firm* — Cooley LLP

(57) ABSTRACT

A novel garden bean cultivar, designated H37113, is disclosed. The invention relates to the seeds of garden bean cultivar H37113, to the plants of garden bean line H37113 and to methods for producing a bean plant by crossing the cultivar H37113 with itself or another bean line. The invention further relates to methods for producing a bean plant containing in its genetic material one or more transgenes and to the transgenic plants produced by that method and to methods for producing other garden bean lines derived from the cultivar H37113.

20 Claims, No Drawings

GARDEN BEAN CULTIVAR H37113

FIELD OF THE INVENTION

The present invention relates to a new and distinctive garden bean cultivar (*Phaseolus vulgaris*) designated H37113.

BACKGROUND OF THE INVENTION

The disclosures, including the claims, figures and/or drawings, of each and every patent, patent application, and publication cited herein are hereby incorporated herein by reference in their entireties.

The following description includes information that may be useful in understanding the present invention. It is not an admission that any of the information provided herein is prior art or relevant to the presently claimed inventions, or that any publication specifically or implicitly referenced is prior art.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm.

In beans, these important traits may include fresh pod yield, higher seed yield, resistance to diseases and insects, better stems and roots, tolerance to drought and heat, and better agronomic quality. With mechanical harvesting of many crops, uniformity of plant characteristics such as germination and stand establishment, growth rate, maturity and plant height is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, recurrent selection and backcross breeding.

The complexity of inheritance influences choice of the breeding method. Backcross breeding is used to transfer one or a few favorable genes for a highly heritable trait into a desirable cultivar. This approach has been used extensively for breeding disease-resistant cultivars. Nevertheless, it is also suitable for the adjustment and selection of morphological character, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars. Those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and/or to a widely grown standard cultivar. If a single observation is inconclusive, replicated observations provide a better estimate of its genetic worth.

The goal of garden bean plant breeding is to develop new, unique and superior garden bean cultivars. The breeder initially selects and crosses two or more parental lines, followed by repeated selfing and selection, producing many new genetic combinations. The breeder can theoretically generate billions of different genetic combinations via crossing, selfing and mutations.

Each year, the plant breeder selects the germplasm to advance to the next generation. This germplasm is grown under unique and different geographical, climatic and soil conditions and further selections are then made during and at the end of the growing season. The cultivars that are developed are unpredictable. This unpredictability is because the breeder's selection occurs in unique environments with no control at the DNA level (using conventional breeding procedures), and with millions of different possible genetic combinations being generated. A breeder of ordinary skill in the art cannot predict the final resulting lines he develops, except possibly in a very gross and general fashion. This unpredictability results in the expenditure of large amounts of research monies to develop superior new garden bean cultivars.

The development of new garden bean cultivars requires the development and selection of garden bean varieties, the crossing of these varieties and the evaluation of the crosses.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes.

Pedigree breeding is used commonly for the improvement of self-pollinating crops or inbred lines of cross-pollinating crops. Two parents that possess favorable, complementary traits are crossed to produce an $F_1$. An $F_2$ population is produced by selfing one or several $F_1$s or by intercrossing two $F_1$s (sib mating). Selection of the best individuals may begin in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, garden bean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987; Principles of Crop Development, Macmillan Publishing Co.; N. F. Jensen, 1988, Plant Breeding Methodology, John Wiley & Sons).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Garden bean, *Phaseolus vulgaris* L., is an important and valuable vegetable crop. Thus, a continuing goal of garden bean plant breeders is to develop stable, high yielding garden bean cultivars that are agronomically sound. The reasons for this goal are obviously to maximize the amount of yield produced on the land. To accomplish this goal, the garden bean breeder must select and develop garden bean plants that have traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a novel garden bean cultivar designated H37113. This invention thus relates to the seeds of garden bean cultivar H37113, to the plants or part(s) thereof of garden bean cultivar H37113, to plants or part(s) thereof consisting essentially of the phenotypic and morphological characteristics of garden bean cultivar H37113, and/or having all the phenotypic and morphological characteristics of garden bean cultivar H37113, and/or having the phenotypic and morphological characteristics of garden bean cultivar H37113 listed in Table 1, including but not limited to as determined at the 5% significance level when grown in the same environmental conditions. The invention also relates to variants, mutants and trivial modifications of the seed or plant of garden bean cultivar H37113. Plant parts of the garden bean cultivar of the present invention are also provided such as, i.e., pollen obtained from the plant cultivar and an ovule obtained from the plant cultivar.

The plants and seeds of the present invention include those that may be of an essentially derived variety as defined in section 41(3) of the Plant Variety Protection Act, i.e., a variety that:

(i) is predominantly derived from garden bean cultivar H37113 or from a variety that is predominantly derived from garden bean cultivar H37113, while retaining the expression of the essential characteristics that result from the genotype or combination of genotypes of garden bean cultivar H37113;

(ii) is clearly distinguishable from garden bean cultivar H37113; and (iii) except for differences that result from the act of derivation, conforms to the initial variety in the expression of the essential characteristics that result from the genotype or combination of genotypes of the initial variety.

In another aspect, the present invention provides regenerable cells for use in tissue culture of bean cultivar H37113. The tissue culture will preferably be capable of regenerating plants consisting essentially of the phenotypic and morphological characteristics of garden bean cultivar H37113 and/or having all the phenotypic and morphological characteristics of garden bean cultivar H37113, and/or having the physiological and morphological characteristics of bean cultivar H37113. Preferably, the cells of such tissue culture will be embryos, meristematic cells, seeds, callus, pollen, leaves, anthers, pistils, roots, root tips, pods, flowers and stems. Protoplasts produced from such tissue culture are also included in the present invention. The bean shoots, roots and whole plants regenerated from the tissue culture are also part of the invention.

Also included in the invention are methods for producing a bean plant produced by crossing bean cultivar H37113 with itself or another bean cultivar. When crossed with itself, i.e., when crossed with another bean cultivar H37113 plant or self-pollinated, bean cultivar H37113 will be conserved (e.g., as an inbred). When crossed with another, different bean plant, an $F_1$ hybrid seed is produced. $F_1$ hybrid seeds and plants produced by growing said hybrid seeds are included in the present invention. A method for producing an $F_1$ hybrid bean seed comprising crossing a bean cultivar H37113 plant with a different bean plant and harvesting the resultant hybrid bean seed are also part of the invention. The hybrid bean seed produced by the method comprising crossing a bean cultivar H37113 plant with a different bean plant and harvesting the resultant hybrid bean seed, are included in the invention, as are the hybrid bean plant or part(s) thereof, and seeds produced by growing said hybrid bean seed.

In another aspect, the present invention provides transformed H37113 bean cultivar plants or part(s) thereof that have been transformed so that its genetic material contains one or more transgenes, preferably operably linked to one or more regulatory elements. Also, the invention provides methods for producing a bean plant containing in its genetic material one or more transgenes, preferably operably linked to one or more regulatory elements, by crossing transformed H37113 bean cultivar plants with either a second plant of another bean cultivar, or a non-transformed H37113 bean cultivar, so that the genetic material of the progeny that results from the cross contains the transgene(s), preferably operably linked to one or more regulatory elements. The invention also provides methods for producing a bean plant that contains in its genetic material one or more transgene(s), wherein the method comprises crossing the cultivar H37113 with a second bean cultivar of another bean cultivar which contains one or more transgene(s) operably linked to one or more regulatory element(s) so that the genetic material of the progeny that results from the cross contains the transgene(s) operably linked to one or more regulatory element(s). Transgenic bean cultivars, or part(s) thereof produced by the methods are in the scope of the present invention.

More specifically, the invention comprises methods for producing a male sterile bean plant, an herbicide resistant bean plant, an insect resistant bean plant, a disease resistant bean plant, a water stress tolerant bean plant, a heat stress tolerant bean plant, and a bean plant with improved shelf-life. Said methods comprise transforming a bean cultivar H37113 plant with a nucleic acid molecule that confers, for example, male sterility, herbicide resistance, insect resistance, disease resistance, water stress tolerance, heat stress tolerance, or improved shelf life, respectively. The transformed bean plants, or part(s) thereof, obtained from the provided methods, including, for example, a male sterile bean plant, an herbicide resistant bean plant, an insect resistant bean plant, a disease resistant bean plant, a bean plant tolerant to water stress, a bean plant tolerant to heat stress or a bean plant with improved shelf-life are included in the present invention. For the present invention and the skilled artisan, disease is understood to be fungal diseases, viral diseases, bacterial diseases or other plant pathogenic diseases and a disease resistant plant will encompass a plant resistant to fungal, viral, bacterial and other plant pathogens.

In another aspect, the present invention provides for methods of introducing one or more desired trait(s) into bean cultivar H37113 and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance to bacterial, fungal, or viral disease, increased leaf number, improved shelf-life, and tolerance to water stress or heat stress. The gene or genes may be naturally occurring gene(s) or transgene(s) introduced through genetic engineering techniques. The method for introducing the desired trait(s) is preferably a backcrossing process making use of a series of backcrosses to bean cultivar H37113 during which the desired trait(s) is maintained by selection.

When using a transgene, the trait is generally not incorporated into each newly developed line/cultivar such as bean cultivar H37113 by direct transformation. Rather, the more typical method used by breeders of ordinary skill in the art to incorporate the transgene is to take a line already carrying the transgene and to use such line as a donor line to transfer the transgene into the newly developed line. The same would apply for a naturally occurring trait or one arising from spontaneous or induced mutations. The backcross breeding process comprises the following steps: (a) crossing bean cultivar H37113 plants with plants of another cultivar that comprise the desired trait(s); (b) selecting the $F_1$ progeny plants that have the desired trait(s); (c) crossing the selected $F_1$ progeny plants with bean cultivar H37113 plants to produce backcross progeny plants; (d) selecting for backcross progeny plants that have the desired trait(s) and physiological and morphological characteristics of bean cultivar H37113 to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that consist essentially of the phenotypic and morphological characteristics of garden bean cultivar H37113, and/or have all the phenotypic and morphological characteristics of garden bean cultivar H37113, and/or have the desired trait(s) and the physiological and morphological characteristics of bean cultivar H37113 as determined in Table 1, including but not limited to, at a 5% significance level when grown in the same environmental conditions. The bean plants produced by the methods are also part of the invention. Backcrossing breeding methods, well-known for one skilled in the art of plant breeding, will be further developed in subsequent parts of the specification.

In a preferred embodiment, the present invention provides methods for increasing and producing bean cultivar H37113 seed, whether by crossing a first parent bean cultivar plant with a second parent bean cultivar plant and harvesting the resultant bean seed, wherein both said first and second parent bean cultivar plant are the bean cultivar H37113 or by planting a bean seed of the bean cultivar H37113, growing a bean cultivar H37113 plant from said seed, controlling a self pollination of the plant where the pollen produced by a grown bean cultivar H37113 plant pollinates the ovules produced by the very same bean cultivar H37113 grown plant, and harvesting the resultant seed.

The invention further provides methods for developing bean cultivars in a bean breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, bean plants, and part(s) thereof produced by such breeding methods are also part of the invention.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bean yield (tons/acre). The yield in tons/acre is the actual yield of the bean pods at harvest.

Determinate plant. A determinate plant will grow to a fixed number of nodes while an indeterminate plant continues to grow during the season.

Emergence. The rate that the seed germinates and sprouts out of the ground.

Essentially all the physiological and morphological characteristics. A plant having essentially all the physiological and morphological characteristics means a plant having the physiological and morphological characteristics, except for the characteristics derived from the converted gene.

Field holding ability. A bean plant that has field holding ability means a plant having pods that remain smooth and retain their color even after the seed is almost fully developed.

Immunity to disease(s) and or insect(s). A bean plant which is not subject to attack or infection by specific disease(s) and or insect(s) is considered immune.

Intermediate resistance to disease(s) and or insect(s). A bean plant that restricts the growth and development of specific disease(s) and or insect(s), but may exhibit a greater range of symptoms or damage compared to resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant bean plants are not immune to the disease(s) and or insect(s).

Machine harvestable bush. A machine harvestable bush means a bean plant that stands with pods off the ground. The pods can be removed by a machine from the plant without leaves and other plant parts.

Maturity. A maturity under 53 days is considered early while maturity between 54-59 days is considered average or medium and maturity of 60 or more days would be late.

Maturity date. Plants are considered mature when the pods have reached their maximum allowable seed size and sieve size for the specific use intended. This can vary for each end user, e.g., processing at different stages of maturity would be required for different types of consumer beans, such as "whole pack," "cut," or "french style." The number of days are calculated from a relative planting date which depends on day length, heat units, and other environmental factors.

Plant adaptability. A plant having good plant adaptability means a plant that will perform well in different growing conditions and seasons.

Plant architecture. Plant architecture is the shape of the overall plant which can be tall-narrow, short-wide, medium height, and/or medium width.

Plant cell. As used herein, the term "plant cell" includes plant cells whether isolated, in tissue culture, or incorporated in a plant or plant part.

Plant habit. A plant can be erect (upright) to sprawling on the ground.

Plant height. Plant height is taken from the top of the soil to the top node of the plant and is measured in centimeters or inches.

Plant part. As used herein, the term "plant part" includes any part of the plant including but not limited to leaves, stems, roots, seed, embryos, pollen, ovules, flowers, root tips, anthers, tissue, cells, pods, and the like.

Pod set height. The pod set height is the location of the pods within the plant. The pods can be high (near the top), low (near the bottom), or medium (in the middle) of the plant.

Regeneration. Regeneration refers to the development of a plant from tissue culture.

Resistance to disease(s) and or insect(s). A bean plant that restricts the growth and development of specific disease(s) and or insect(s) under normal disease(s) and or insect(s) attack pressure when compared to susceptible plants. These bean plants can exhibit some symptoms or damage under heavy disease(s) and or insect(s) pressure. Resistant bean plants are not immune to the disease(s) and or insect(s).

RHS. RHS refers to the Royal Horticultural Society of England which publishes an official botanical color chart quantitatively identifying colors according to a defined numbering system. The chart may be purchased from Royal Hort. Society Enterprise Ltd. RHS Garden; Wisley, Woking, Surrey GU236QB, UK.

Sieve size (sv). Sieve size 1 means pods that fall through a sieve grader which culls out pod diameters of 4.76 mm through 5.76 mm. Sieve size 2 means pods that fall through a sieve grader which culls out pod diameters of 5.76 mm through 7.34 mm. Sieve size 3 means pods that fall through a sieve grader which culls out pod diameters of 7.34 mm through 8.34 mm. Sieve size 4 means pods that fall through a sieve grader which culls out pod diameters of 8.34 mm through 9.53 mm. Sieve size 5 means pods that fall through a sieve grader which culls out pod diameters of 9.53 mm through 10.72 mm. Sieve size 6 means pods that fall through a sieve grader that will cull out pod diameters of 10.72 mm or larger.

Single gene converted (conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Slow seed development. Beans having slow seed development develop seed slowly even after the pods are full sized. This characteristic gives to the cultivar its field holding ability.

Susceptible to disease(s) and or insect(s). A bean plant that is susceptible to disease(s) and or insect(s) is defined as a bean plant that has the inability to restrict the growth and development of specific disease(s) and or insect(s). Plants that are susceptible will show damage when infected and are more likely to have heavy damage under moderate levels of specific disease(s) and or insect(s).

DETAILED DESCRIPTION OF THE INVENTION

Garden bean cultivar H37113 has superior characteristics and was developed from an initial cross that was made in San Juan Bautista (SJB), Calif., in a greenhouse, in the fall. In the first year of development, the cross was made between two proprietary lines under stake numbers M7156 (female) and M7005 (male), the $F_1$ generation was harvested in March near Los Mochis, Mexico, in plot 9N3331, and the $F_2$ selection was made in July near Coloma, Wis., in plot 9Y2341. In the second year, the $F_3$ selection was made in March near Immokalee, Fla., in plot F49098 and the $F_4$ selection was made in August near Sun Prairie, Wis., in plot W410621. In the third year, the $F_5$ selection was made in March near Immokalee, Fla., in plot F500296 and the $F_6$ generation was bulk harvested in August in SJB, Calif., in plot C510244. In the fourth year, the $F_7$ generation was bulk harvested in August in SJB, Calif., in plot C604285. In the fifth year, the $F_8$ generation was bulked in February near Los Mochis, Mexico, in plot M74301-320. The line was subsequently designated H37113.

Garden bean cultivar H37113 is similar to garden bean cultivar 'Ambra'. While similar to garden bean cultivar 'Ambra', there are significant differences including garden bean cultivar H37113 has Resistant to *Uromyces appendiculatus*: (rust races 38, 53 and 72), while garden bean cultivar 'Ambra' is susceptible. In addition, garden bean cultivar H37113 is three days later to edible maturity than cultivar 'Ambra'. The pods of H37113 are darker green than the pods of 'Ambra'.

Garden bean cultivar H37113 is a 55-day medium maturity bean with uniform medium dark green pods on an upright plant structure (habit). The pods are very straight and smooth and are borne in the upper one-half of the plant. The majority of the pods are in the 4 sieve range. The leaves are medium in size with a medium-dark green, semi-glossy color. Garden bean cultivar H37113 is a determinate plant and is resistant to Bean Common Mosaic Virus (BCMV I-gene),) and *Uromyces appendiculatus*: (rust races 38, 53 and 72). In addition, garden bean cultivar H37113 also has intermediate resistance to Beet Curly Top Virus (BCTV) and *Psuedomonas syringae* pv syringae (Bacterial brown spot).

Some of the selection criteria used for various generations include: pod appearance and length, bean yield, pod set height, emergence, maturity, plant architecture, habit and height, seed yield, and quality and disease resistance.

Bean Common Mosaic Virus resistance is a desired trait for a bean variety. The disease occurs worldwide causing low quality of the harvest product and losses from 80% to 100% by reduction of yield. It is mostly transmitted by aphids during the growing season, but can also be spread by pollen or mechanically. The leaves develop mosaic patterns in which irregular light and dark green patches are intermixed. Malformation and yellow dots may also be produced, often causing growth reduction. The plant may be dwarfed and pod and seed yield reduced. Severe necrosis may occur and the plant may die if infected while young. Systemic necrosis, in which the roots and shoots become blackened, appears in cultivars having a dominant resistance gene (hypersensitive resistance mechanism). The systemic necrosis may spread to higher leaves without killing them or may be concentrated in the vascular parts of the stem, eventually leading to the death of all or part of the plant. When infection occurs late in plant development, parts of the plant may die and many pods may show brown discoloration in the pod wall and pod suture as a result of vascular necrosis.

Garden bean cultivar H37113 has shown uniformity and stability for the traits, as described in the following Variety Description Information. It has been self-pollinated a sufficient number of generations with careful attention to uniformity of plant type. The cultivar has been increased with continued observation for uniformity. No variant traits have been observed or are expected for agronomically important traits in garden bean cultivar H37113.

Garden bean cultivar H37113 has the following morphologic and other characteristics (based primarily on data collected at Immokalee, Fla., Crossville, Tenn., and Sun Prairie, Wis.).

TABLE 1

VARIETY DESCRIPTION INFORMATION

| | |
|---|---|
| Market Maturity: | |
| Days to edible pods: | 55 |
| Number of days later than 'Ambra': | 3 |
| Plant: | |
| Habit: | Determinate |
| Height: | 43.0 cm, taller than 'Ambra' by 0.0 cm |
| Spread: | 46.0 cm, narrower than 'Ambra' by 1.0 cm |
| Pod position: | High |
| Bush form: | High Bush |
| Leaves: | |
| Surface: | Semi-glossy |
| Size: | Medium |
| Color: | Medium dark-green |
| Anthocyanin Pigment: | |
| Flowers: | Absent |
| Stems: | Absent |
| Pods: | Absent |
| Seeds: | Absent |
| Leaves: | Absent |
| Petioles: | Absent |
| Peduncles: | Absent |
| Nodes: | Absent |
| Flower Color: | |
| Color of standard: | White |
| Color of wings: | White |
| Color of keel: | White |
| Pods (edible maturity): | |
| Exterior color: | Medium Dark-green |
| Cross section pod shape: | Round |
| Creaseback: | Present |
| Pubescence: | Moderate |
| Constriction: | None |
| Spur length: | 1.5 cm |
| Fiber: | Considerable |
| Number of seeds/pods: | 6 |
| Suture string: | Absent |
| Seed development: | Slow |
| Machine harvest: | Adapted |
| Distribution of sieve size at optimum maturity: | 25% 7.34 mm to 8.34 mm - Sieve 3<br>75% 8.34 mm to 9.53 mm - Sieve 4 |
| Seed Color: | |
| Seed coat luster: | Shiny |
| Seed coat: | Monochrome |
| Primary color: | White |
| Seed coat pattern: | Solid |
| Hilar ring: | Absent |
| Seed Shape and Size: | |
| Hilum view: | Elliptical |
| Cross section: | Round |
| Side view: | Oval to oblong |
| Seed size (g/100 seeds): | 30; 5 more than 'Ambra' |
| Disease Resistance: | |
| Bean Common Mosaic Virus (BCMV I gene): | Resistant |
| *Pseudomonas savastanoi* pv *phaseolicola* (halo blight): | Intermediate Resistant |
| *Psuedomonas syringae* pv *syringae* (Bacterial Brown Spot): | Intermediate Resistant |
| Beet Curly Top Virus | Intermediate Resistant |

TABLE 1-continued

VARIETY DESCRIPTION INFORMATION (BCTV):
Uromyces appendiculatus: Resistant
(rust races 38, 53 and 72):

FURTHER EMBODIMENTS OF THE INVENTION

This invention also is directed to methods for producing a garden plant by crossing a first parent bean plant with a second parent bean plant wherein either the first or second parent bean plant is a bean plant of the line H37113. Further, both first and second parent bean plants can come from cultivar H37113. When self pollinated, or crossed with another bean cultivar H37113 plant, the bean cultivar H37113 will be stable, while when crossed with another, different bean cultivar plant, an $F_1$ hybrid seed is produced. Such methods of hybridization and self-pollination of the common bean are well known to those skilled in the art of bean breeding. See, for example, F. A. Bliss, 1980, Common Bean, In Hybridization of Crop Plants, Fehr and Hadley, eds., Chapter 17: 273-284, American Society of Agronomy and Crop Science Society of America, Publishers.

Still further, this invention also is directed to methods for producing an H37113-derived bean plant by crossing cultivar H37113 with a second bean plant and growing the progeny seed, and repeating the crossing and growing steps with the cultivar H37113-derived plant from 0 to 7 times. Thus, any such methods using the cultivar H37113 are part of this invention: selfing, backcrosses, hybrid production, crosses to populations, and the like. All plants produced using cultivar H37113 as a parent are within the scope of this invention, including plants derived from cultivar H37113. Advantageously, the cultivar is used in crosses with other, different, cultivars to produce first generation ($F_1$) bean seeds and plants with superior characteristics.

As used herein, the term "plant" includes plant cells, plant protoplasts, plant cell tissue cultures from which garden bean plants can be regenerated, plant calli, plant clumps and plant cells that are intact in plants or parts of plants, such as embryos, pollen, ovules, flowers, seeds, pods, stems, roots, anthers, pistils, root tips, leaves, and the like.

As is well known in the art, tissue culture of garden bean can be used for the in vitro regeneration of a garden bean plant. Tissue culture of various tissues of garden beans and regeneration of plants therefrom is well known and widely published. For example, reference may be had to McClean, P., Grafton, K. F., "Regeneration of dry bean (*Phaseolus vulgaris*) via organogenesis," *Plant Sci.*, 60, 117-122 (1989); Mergeai, G., Baudoin, J. P., "Development of an in vitro culture method for heart-shaped embryo in *Phaseolus vulgaris*," B.I.C. Invit. Papers 33, 115-116 (1990); Vanderwesthuizen, A. J., Groenewald, E. G., "Root Formation and Attempts to Establish Morphogenesis in Callus Tissues of Beans (*Phaseolus-vulgaris* L.)," *S. Afr. J. Bot.* 56, 271-273 (2 Apr. 1990); Benedicic, D., et al., "The regeneration of *Phaseolus vulgaris* L. plants from meristem culture," Abst. 5th I.A.P.T.C. Cong. 1, 91 (#A3-33) (1990); Genga, A., Allavena, A., "Factors affecting morphogenesis from immature cotyledons of *Phaseolus coccineus* L.," Abst. 5th I.A.P.T.C. Cong. 1, 101 (#A3-75) (1990); Vaquero, F., et al., "Plant regeneration and preliminary studies on transformation of *Phaseolus coccineus*," Abst. 5th I.A.P.T.C. Cong. 1, 106 (#A3-93) (1990); Franklin, C. I., et al., "Plant Regeneration from Seedling Explants of Green Bean (*Phaseolus-Vulgaris* L.) via Organogenesis," *Plant Cell Tissue Org. Cult.*, 24, 199-206 (3 Mar. 1991); Malik, K. A., Saxena, P. K., "Regeneration in *Phaseolus-vulgaris* L.—Promotive Role of N6-Benzylaminopurine in Cultures from Juvenile Leaves," *Planta*, 184(1), 148-150 (1991); Genga, A., Allavena, A., "Factors affecting morphogenesis from immature cotyledons of *Phaseolus coccineus* L.," *Plant Cell Tissue Org. Cult.*, 27, 189-196 (1991); Malik, K. A., Saxena, P. K., "Regeneration in *Phaseolus vulgaris* L.—High-Frequency Induction of Direct Shoot Formation in Intact Seedlings by N-6-Benzylaminopurine and Thidiazuron," 186, 384-389 (3 Feb. 1992); Malik, K. A., Saxena, P. K., "Somatic Embryogenesis and Shoot Regeneration from Intact Seedlings of *Phaseolus acutifolius* A., *P. aureus* (L.) Wilczek, *P. coccineus* L., and *P. wrightii* L.," *Pl. Cell. Rep.*, 11, 163-168 (3 Apr. 1992); Chavez, J., et al., "Development of an in vitro culture method for heart shaped embryo in *Phaseolus polyanthus*," B.I.C. Invit. Papers 35, 215-216 (1992); Munoz-Florez, L. C., et al., "Finding out an efficient technique for inducing callus from *Phaseolus* microspores," B.I.C. Invit. Papers 35, 217-218 (1992); Vaquero, F., et al., "A Method for Long-Term Micropropagation of *Phaseolus coccineus* L.," *L. Pl. Cell. Rep.*, 12, 395-398 (7-8 May 1993); Lewis, M. E., Bliss, F. A., "Tumor Formation and beta-Glucuronidase Expression in *Phaseolus vulgaris* L. Inoculated with *Agrobacterium Tumefaciens*," *Journal of the American Society for Horticultural Science*, 119, 361-366 (2 Mar. 1994); Song, J. Y., et al., "Effect of auxin on expression of the isopentenyl transferase gene (ipt) in transformed bean (*Phaseolus vulgaris* L.) single-cell clones induced by *Agrobacterium tumefaciens* C58," *J. Plant Physiol.* 146, 148-154 (1-2 May 1995). It is clear from the literature that the state of the art is such that these methods of obtaining plants are routinely used and have a very high rate of success. Thus, another aspect of this invention is to provide cells which upon growth and differentiation produce bean plants having the physiological and morphological characteristics of garden bean cultivar H37113.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed garden bean plants using transformation methods as described below to incorporate transgenes into the genetic material of the garden bean plant(s).

Expression Vectors for Garden Bean Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986)). Other selectable marker genes confer resistance to herbicides such as glyphosate, glufosinate or bromoxynil (Comai, et al., *Nature*, 317:741-744 (1985); Gordon-Kamm, et al., *Plant Cell*, 2:603-618 (1990); and Stalker, et al., *Science*, 242:419-423 (1988)).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

In vivo methods for visualizing GUS activity that do not require destruction of plant tissue are available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells (Chalfie, et al., *Science*, 263:802 (1994)). GFP and mutants of GFP may be used as screenable markers.

Expression Vectors for Garden bean Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in garden bean. Optionally, the inducible promoter is operably linked to a nucleotide sequence encoding a signal sequence which is operably linked to a gene for expression in garden bean. With an inducible promoter the rate of transcription increases in response to an inducing agent.

Any inducible promoter can be used in the instant invention. See, Ward, et al., *Plant Mol. Biol.*, 22:361-366 (1993). Exemplary inducible promoters include, but are not limited to, that from the ACEI system which responds to copper (Mett, et al., *Proc. Natl. Acad. Sci. USA*, 90:4567-4571 (1993)); In2 gene from maize which responds to benzenesulfonamide herbicide safeners (Gatz, et al., *Mol. Gen. Genetics*, 243:32-38 (1994)), or Tet repressor from Tn10 (Gatz, et al., *Mol. Gen. Genetics*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *Proc. Natl. Acad. Sci. USA*, 88:0421 (1991)).

B. Constitutive Promoters—A constitutive promoter is operably linked to a gene for expression in garden bean or the constitutive promoter is operably linked to a nucleotide sequence encoding a signal sequence which is operably linked to a gene for expression in garden bean.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell* 2, 163-171 (1990)); ubiquitin (Christensen, et al., *Plant Mol. Biol.,* 12:619-632 (1989) and Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)) and maize H3 histone (Lepetit, et al., *Mol. Gen. Genetics,* 231: 276-285 (1992) and Atanassova, et al., *Plant Journal,* 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See, PCT Application WO 96/30530.

C. Tissue-specific or Tissue-preferred Promoters—A tissue-specific promoter is operably linked to a gene for expression in garden bean. Optionally, the tissue-specific promoter is operably linked to a nucleotide sequence encoding a signal sequence which is operably linked to a gene for expression in garden bean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., *Science,* 23:476-482 (1983) and Sengupta-Gopalan, et al., *Proc. Natl. Acad. Sci. USA* 82:3320-3324 (1985)); a leaf-specific and light-induced promoter such as that from cab or rubisco (Simpson, et al., *EMBO J.,* 4(11): 2723-2729 (1985) and Timko, et al., *Nature,* 318:579-582 (1985)); an anther-specific promoter such as that from LAT52 (Twell, et al., *Mol. Gen. Genetics,* 217:240-245 (1989)); a pollen-specific promoter such as that from Zm13 or a microspore-preferred promoter such as that from apg (Twell, et al., *Sex. Plant Reprod.,* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Knox, C., et al., "Structure and Organization of Two Divergent Alpha-Amylase Genes from Barley," *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., Plant J., 2:129 (1991); Kalderon, et al., Cell, 39:499-509 (1984); Steifel, et al., "Expression of a maize cell wall hydroxyproline-rich glycoprotein gene in early leaf and root vascular differentiation," *Plant Cell,* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is a garden bean plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see *Methods in Plant Molecular Biology and Biotechnology,* Glick and Thompson Eds., CRC Press, Inc., Boca Raton, 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defences are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., *Science,* 266:789 (1994) (cloning of the tomato Cf-9 gene for resistance to *Cladosporium fulvum*); Martin, et al., *Science,* 262:1432 (1993) (tomato Pto gene for resistance to *Pseudomonas syringae* pv. tomato encodes a protein kinase); Mindrinos, et al., *Cell,* 78:1089 (1994) (*Arabidopsis* RSP2 gene for resistance to *Pseudomonas syringae*).

B. A *Bacillus thuringiensis* protein, a derivative thereof or a synthetic polypeptide modelled thereon. See, for example, Geiser, et al., *Gene,* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, Van Damme, et al., *Plant Molec. Biol.,* 24:25 (1994), who disclose the nucleotide sequences of several *Clivia miniata* mannose-binding lectin genes.

D. A vitamin-binding protein such as avidin. See, PCT Application US 93/06487 which teaches the use of avidin and avidin homologues as larvicides against insect pests.

E. An enzyme inhibitor, for example, a protease or proteinase inhibitor or an amylase inhibitor. See, for example, Abe, et al., *J. Biol. Chem.*, 262:16793 (1987) (nucleotide sequence of rice cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor).

F. An insect-specific hormone or pheromone such as an ecdysteroid or juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosure of Pratt, et al., *Biochem. Biophys. Res. Comm.*, 163:1243 (1989) (an allostatin is identified in *Diploptera puntata*). See also, U.S. Pat. No. 5,266,317 to Tomalski, et al., which discloses genes encoding insect-specific, paralytic neurotoxins.

H. An insect-specific venom produced in nature by a snake, a wasp, etc. For example, see Pang, et al., *Gene*, 116:165 (1992), for disclosure of heterologous expression in plants of a gene coding for a scorpion insectotoxic peptide.

I. An enzyme responsible for a hyperaccumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott, et al.), which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene.

K. A molecule that stimulates signal transduction. For example, see the disclosure by Botella, et al., *Plant Molec. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

L. A hydrophobic moment peptide. See, PCT Application WO 95/16776, which discloses peptide derivatives of tachyplesin which inhibit fungal plant pathogens, and PCT Application WO 95/18855, which teaches synthetic antimicrobial peptides that confer disease resistance.

M. A membrane permease, a channel former, or a channel blocker. For example, see the disclosure of Jaynes, et al., *Plant Sci*, 89:43 (1993), of heterologous expression of a cecropin-βlytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus and tobacco streak virus, potato virus X, potato virus Y, tobacco etch virus, tobacco rattle virus, and tobacco mosaic virus. Id.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki, et al., *Nature*, 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilising plant cell wall homo-α-1,4-D-galacturonase. See, Lamb, et al., *Bio/Technology*, 10:1436 (1992).

R. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., "Plant disease resistance. Grand unification system theory in sight," *Current Biology*, 5(2) (1995).

T. Antifungal genes. See, Cornelissen and Melchers, "Strategies for Control of Fungal Diseases with Transgenic Plants," *Plant Physiol.*, 101:709-712 (1993); and Bushnell, et al., "Genetic Engineering of Disease Resistance in Cereal," *Can. J. of Plant Path.*, 20(2):137-149 (1998).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988), and Miki, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada, et al., and U.S. Pat. No. 4,975,374 to Goodman, et al., disclose nucleotide sequences of glutamine synthetase genes which confer resistance to herbicides such as L-phosphinothricin. See also, Russel, D. R., et al., *Plant Cell Report*, 12:3 165-169 (1993). The nucleotide sequence of a phosphinothricin-acetyl-transferase (PAT) gene is provided in European Application No. 0 242 246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc2-S3 genes described by Marshall, et al., *Theor. Appl. Genet.*, 83:435 (1992).

C. An herbicide that inhibits photosynthesis, such as a triazine (psbA and gs+ genes) and a benzonitrile (nitrilase gene). Przibila, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992).

D. Acetohydroxy acid synthase, which has been found to make plants that express this enzyme resistant to multiple types of herbicides, has been introduced into a variety of plants. See, Hattori, et al., "An Acetohydroxy acid synthase mutant reveals a single site involved in multiple herbicide resistance," *Mol. Gen. Genet.,* 246:419-425 (1995). Other genes that confer tolerance to herbicides include a gene encoding a chimeric protein of rat cytochrome P4507A1 and yeast NADPH-cytochrome P450 oxidoreductase (Shiota, et al., "Herbicide-resistant Tobacco Plants Expressing the Fused Enzyme between Rat Cytochrome P4501A1 (CYP1A1) and Yeast NADPH-Cytochrome P450 Oxidoreductase," *Plant Physiol.,* 106:17 (1994)), genes for glutathione reductase and superoxide dismutase (Aono, et al., "Paraquat tolerance of transgenic *Nicotiana tabacum* with enhanced activities of glutathione reductase and superoxide dismutase," *Plant Cell Physiol.,* 36:1687 (1995)), and genes for various phosphotransferases (Datta, et al., "Herbicide-resistant Indica rice plants from IRRI breeding line IR72 after PEG-mediated transformation of protoplants," *Plant Mol. Biol.,* 20:619 (1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

3. Genes that Confer or Contribute to a Value-Added Trait, Such as:

A. Delayed and attenuated symptoms to Bean Golden Mosaic Geminivirus (BGMV), for example, by transforming a plant with antisense genes from the Brazilian BGMV. See, Arago, et al., *Molecular Breeding,* 4:6, 491-499 (1998).

B. Increased the bean content in Methionine by introducing a transgene coding for a Methionine rich storage albumin (2S-albumin) from the Brazil nut as described in Arago, et al., *Genetics and Molecular Biology.,* 22:3, 445-449 (1999).

Methods for Garden Bean Transformation

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium.* See, for example, Horsch, et al., *Science,* 227:1229 (1985); Diant, et al., Molecular Breeding, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports,* 8:238 (1989). See also, U.S. Pat. No. 5,591,616 issued Jan. 7, 1997.

B. Direct Gene Transfer—Despite the fact the host range for *Agrobacterium*-mediated transformation is broad, some cereal or vegetable crop species and gymnosperms have generally been recalcitrant to this mode of gene transfer, even though some success has been achieved in rice and corn. Hiei, et al., *The Plant Journal,* 6:271-282 (1994) and U.S. Pat. No. 5,591,616 issued Jan. 7, 1997. Several methods of plant transformation, collectively referred to as direct gene transfer, have been developed as an alternative to *Agrobacterium-*mediated transformation. A generally applicable method of plant transformation is microprojectile-mediated transformation where DNA is carried on the surface of microprojectiles measuring 1 to 4 microns. The expression vector is introduced into plant tissues with a biolistic device that accelerates the microprojectiles to speeds of 300 to 600 m/s which is sufficient to penetrate plant cell walls and membranes. Russell, D. R., et al., *Pl. Cell. Rep.,* 12, 165-169 (3 Jan. 1993); Aragao, F. J. L., et al., *Plant Mol. Biol.,* 20, 357-359 (2 Oct. 1992); Aragao, *Theor. Appl. Genet.,* 93:142-150 (1996); Kim, J.; Minamikawa, T., *Plant Science,* 117:131-138 (1996); Sanford, et al., *Part. Sci. Technol.,* 5:27 (1987); Sanford, J. C., *Trends Biotech.,* 6:299 (1988); Klein, et al., *Bio/Tech.,* 6:559-563 (1988); Sanford, J. C., *Physiol Plant,* 7:206 (1990); Klein, et al., *Biotechnology,* 10:268 (1992).

Another method for physical delivery of DNA to plants is sonication of target cells. Zhang, et al., *Bio/Technology,* 9:996 (1991). Alternatively, liposome and spheroplast fusion have been used to introduce expression vectors into plants. Deshayes, et al., *EMBO J.,* 4:2731 (1985); Christou, et al., *Proc Natl. Acad. Sci. USA,* 84:3962 (1987). Direct uptake of DNA into protoplasts using $CaCl_2$ precipitation, polyvinyl alcohol or poly-L-ornithine have also been reported. Hain, et al., *Mol. Gen. Genet.,* 199:161 (1985) and Draper, et al., *Plant Cell Physiol.,* 23:451 (1982). Electroporation of protoplasts and whole cells and tissues have also been described Saker, M. and Kuhne, T., *Biologia Plantarum,* 40(4):507-514 (1997/98); D'Halluin, et al., *Plant Cell,* 4:1495-1505 (1992); and Spencer, et al., *Plant Mol. Biol.,* 24:51-61 (1994)).

Following transformation of garden bean target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular garden bean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Backcrossing

When the term garden bean plant, cultivar or bean line are used in the context of the present invention, this also includes cultivars where one or more desired traits has been introduced through backcrossing methods, whether such trait is a naturally occurring one or a transgenic one. Backcrossing methods can be used with the present invention to improve or introduce a characteristic into the line. The term "backcrossing" as used herein refers to the repeated crossing of a hybrid progeny back to the recurrent parent, i.e., backcrossing one, two, three, four, five, six, seven, eight, nine, or more times to the recurrent parent. The parental bean plant which contributes the gene for the desired characteristic is termed the nonrecurrent or donor parent. This terminology refers to the fact that the nonrecurrent parent is used one time in the backcross protocol and therefore does not recur. The parental bean plant to which the gene or genes from the nonrecurrent parent are transferred is known as the recurrent parent as it is used for several rounds in the backcrossing protocol.

In a typical backcross protocol, the original cultivar of interest (recurrent parent) is crossed to a second line (nonrecurrent parent) that carries the gene or genes of interest to be transferred. The resulting progeny from this cross are then crossed again to the recurrent parent and the process is repeated until a garden bean plant is obtained wherein essentially all of the desired morphological and physiological characteristics of the recurrent parent are recovered in the converted plant, generally determined at a 5% significance level when grown in the same environmental condition, in addition to the gene or genes transferred from the nonrecurrent parent. It has to be noted that some, one, two, three, or more, self-pollination and growing of population might be included between two successive backcrosses. Indeed, an appropriate selection in the population produced by the self-pollination, i.e., selection for the desired trait and physiological and morphological characteristics of the recurrent parent might be equivalent to one, two or even three, additional backcrosses in a continuous series without rigorous selection, saving time, money and effort to the breeder. A non limiting example of such a protocol would be the following: (a) the first generation $F_1$ produced by the cross of the recurrent parent A by the donor parent B is backcrossed to parent A; (b) selection is practiced for the plants having the desired trait of parent B; (c) selected plants are self-pollinated to produce a population of plants where selection is practiced for the plants having the desired trait of parent B and the physiological and morphological characteristics of parent A; (d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute a single trait or characteristic in the original line. To accomplish this, a gene or genes of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomical important trait to the plant. The exact backcrossing protocol will depend on the characteristic or trait being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important than the identification of the character(s) in the segregating population. In this instance it may then be necessary to introduce a test of the progeny to determine if the desired characteristic(s) has been successfully transferred. Such tests encompass visual inspection, simple crossing but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele requires selfing the progeny to determine which plant carries the recessive allele(s).

Many single gene traits have been identified that are not regularly selected for in the development of a new line but that can be improved by backcrossing techniques. Single gene traits may or may not be transgenic. Examples of these traits include, but are not limited to, herbicide resistance (such as bar or pat genes), resistance for bacterial, fungal, or viral disease (such as gene I used for BCMV resistance), insect resistance, enhanced nutritional quality (such as 2s albumine gene), industrial usage, agronomic qualities (such as the "persistent green gene"), yield stability, and yield enhancement. These genes are generally inherited through the nucleus. Some other single gene traits are described in U.S. Pat. Nos. 5,777,196, 5,948,957, and 5,969,212, the disclosures of which are specifically hereby incorporated by reference.

In 1981 the backcross method of breeding accounted for 17% of the total breeding effort for inbred corn line development in the United States, according to, Hallauer, A. R., et al., "Corn Breeding," Corn and Corn Improvement, No. 18, pp. 463-481 (1988).

The backcross breeding method provides a precise way of improving varieties that excel in a large number of attributes but are deficient in a few characteristics. (Page 150 of the Pr. R. W. Allard's 1960 book, *Principles of Plant Breeding*, published by John Wiley & Sons, Inc.) The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a variety with exactly the adaptation, yielding ability, and quality characteristics of the recurrent parent but superior to that parent in the particular characteristic(s) for which the improvement program was undertaken. Therefore, this method provides the plant breeder with a high degree of genetic control of his work.

The backcross method is scientifically exact because the morphological and agricultural features of the improved variety could be described in advance and because the same variety could, if it were desired, be bred a second time by retracing the same steps (Briggs, "Breeding wheats resistant to bunt by the backcross method," *Jour. Amer. Soc. Agron.*, 22:289-244 (1930)).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are, for example, the transfer of stem rust resistance from 'Hope' wheat to 'Bart' wheat and even pursuing the backcrosses with the transfer of bunt resistance to create 'Bart 38', having both resistances. Also highlighted by Allard is the successful transfer of mildew, leaf spot and wilt resistances in 'California Common' alfalfa to create 'Caliverde'. This new 'Caliverde' variety produced through the backcross process is indistinguishable from 'California Common' except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, color characteristics, and simply inherited quantitative characters, such as earliness, plant height, and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e., grain size. 'Lady Wright', a long grain variety was used as the donor parent and 'Coloro', a short grain variety as the recurrent parent. After four backcrosses, the medium grain type variety 'Calady' was produced.

DEPOSIT INFORMATION

A deposit of the garden bean seed of this invention is maintained by Harris Moran Seed Company, Sun Prairie Research Station, 1677 Muller Road, Sun Prairie, Wis. 53590. In addition, a sample of the garden bean seed of this invention has been deposited with the National Collections of Industrial, Food and Marine Bacteria (NCIMB), 23 St. Machar Drive, Aberdeen, Scotland, AB24 3RY, United Kingdom.

To satisfy the enablement requirements of 35 U.S.C. 112, and to certify that the deposit of the isolated strain of the present invention meets the criteria set forth in 37 CFR 1.801-1.809, Applicants hereby make the following statements regarding the deposited garden bean cultivar H37113 (deposited as NCIMB Accession No. 41703):

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the effective life of the patent, whichever is longer; and
4. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the NCIMB.

TABLES

In Tables 2 and 3, the traits and characteristics of garden bean cultivar H37113 are compared to the 'Ambra' variety of garden beans. The data was collected during two growing seasons from several field locations in the United States.

The first column shows the variety name.

The second column shows the location of testing. "DMV" indicates DelMarVa; "FL" indicates Florida; "NC" indicates North Carolina; "GA" indicates Georgia; "TN" indicates Tennessee; NJ indicates New Jersey; "spr" indicates springtime; and "fall" indicates fall-time. The number "1", "2", or "3" indicates the first, second, or third planting at the location.

The third column shows the plant height in inches.

The fourth column shows the plant width in inches.

The fifth column indicates the plant habit (structure) with 1=prone (or sprawling) and 9=upright (or erect).

The sixth column indicates the pod length in millimeters.

The seventh column shows the relative pod color with 1=light and 9=dark.

The eighth column shows the pounds of pods harvested from 5 feet of row.

The ninth column shows the relative maturity (the number of days to edible pods).

TABLE 2

Characteristic Comparisons for First Year Field Trials

| Variety | Location | Plant Height | Plant Width | Plant Habit | Pod Length | Pod Color | Yield | Maturity |
|---|---|---|---|---|---|---|---|---|
| Ambra | DMVfall | | | | | 3 | 1.90 | 49 |
| | FLfall | 17 | 20 | 5 | 135 | 3 | 1.40 | |
| | FLfall | 18 | 20 | 5 | 135 | 3 | 1.80 | |
| | FLspr | 15 | 22 | 4 | 150 | 3 | 2.70 | 55 |
| | FLspr | 18 | 21 | 4 | 150 | 3 | 2.20 | 55 |
| | GAspr | 16 | 22 | 4 | 160 | 4 | 2.00 | 56 |
| | NCspr | 15 | 17 | 3 | 120 | 5 | 1.25 | 50 |
| | NCspr | 16 | 20 | 3 | 130 | 5 | 2.25 | 52 |
| | TNfall | 14 | 11 | 5 | 140 | 5 | 1.10 | 56 |
| | TNfall | 15 | 10 | 6 | 140 | 5 | 0.65 | 56 |
| | TNspr | 18 | 16 | 5 | 140 | 4 | 2.20 | 52 |
| | average | 16.2 | 17.9 | 4.4 | 140 | 3.9 | 1.77 | 53.4 |

TABLE 2-continued

Characteristic Comparisons for First Year Field Trials

| Variety | Location | Plant Height | Plant Width | Plant Habit | Pod Length | Pod Color | Yield | Maturity |
|---|---|---|---|---|---|---|---|---|
| 37113 | DMVfall | | | 5 | 130 | 6 | 2.10 | 53 |
| | FLfall | 18 | 20 | 6 | 130 | 5 | 1.50 | |
| | FLfall | 18 | 20 | 6 | 135 | 5 | 1.50 | |
| | FLspr | 18 | 21 | 7 | 145 | 5 | 3.20 | 58 |
| | FLspr | 20 | 21 | 6 | 155 | 5 | 3.00 | 58 |
| | GAspr | 15 | 18 | 6 | 170 | 6 | 1.60 | 58 |
| | NCspr | 19 | 18 | 6 | 140 | 6 | 1.25 | 52 |
| | NCspr | 17 | 17 | 7 | 130 | 6 | 2.00 | 52 |
| | TNfall | 14 | 12 | 7 | 130 | 7 | 0.50 | 58 |
| | TNfall | 13 | 9 | 7 | 150 | 6 | 0.75 | 58 |
| | TNspr | 17 | 16 | 6 | 140 | 5 | 0.50 | 54 |
| | average | 16.9 | 17.2 | 6.3 | 141.4 | 5.6 | 1.63 | 55.7 |

TABLE 3

Characteristic Comparisons for Second Year Field Trials

| Variety | Location | Plant Height | Plant Width | Plant Habit | Pod Length | Pod Color | Yield | Maturity |
|---|---|---|---|---|---|---|---|---|
| Ambra | Flfall | | | 4 | 150 | 3 | 2.70 | 59 |
| | FLspr1 | 16 | 24 | 5 | 150 | 3 | 3.30 | 58 |
| | Flspr3 | 15 | 15 | 5 | 140 | 2 | 1.00 | 59 |
| | NJfall | 15 | 26 | 3 | 150 | 4 | 3.20 | 48 |
| | TNfall1 | 19 | 22 | 6 | 150 | 2 | 3.90 | 52 |
| | TNfall2 | 19 | 20 | 4 | 140 | 3 | 2.60 | 52 |
| | TNspr2 | 16 | 18 | 5 | 140 | 4 | 1.10 | 53 |
| | average | 16.7 | 17.9 | 4.6 | 145.7 | 3 | 2.54 | 54.4 |
| 37113 | Flfall | | | 7 | 145 | 5 | 2.30 | 62 |
| | FLspr1 | 16 | 20 | 7 | 160 | 5 | 2.80 | 58 |
| | Flspr3 | 15 | 17 | 6 | 140 | 5 | 1.20 | 64 |
| | NJfall | 15 | 16 | 6 | 150 | 5 | 2.20 | 52 |
| | TNfall1 | 18 | 19 | 6 | 130 | 4 | 2.30 | 57 |
| | TNfall2 | 16 | 18 | 6 | 130 | 5 | 2.10 | 53 |
| | TNspr2 | 17 | 17 | 6 | 150 | 5 | 0.90 | 57 |
| | average | 16.2 | 17.8 | 6.3 | 143.6 | 4.9 | 1.97 | 57.6 |

The foregoing detailed description has been given for clearness of understanding only and no unnecessary limitations should be understood there from as modifications will be obvious to those skilled in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of bean cultivar designated H37113, wherein a representative sample of seed of said cultivar has been deposited under NCIMB No. 41703.

2. A bean plant, or a part thereof, produced by growing the seed of claim 1.

3. A bean plant, or a part thereof, having all the physiological and morphological characteristics of bean cultivar H37113 listed in Table 1.

4. A bean plant, or a part thereof, having the physiological and morphological characteristics of bean cultivar H37113, wherein a representative sample of seed of said cultivar has been deposited under NCIMB No. 41703.

5. A tissue culture of regenerable cells produced from the plant of claim 2 wherein said cells of the tissue culture are produced from a plant part selected from the group consisting of embryos, meristematic cells, leaves, pollen, root, root tips, stems, anther, pistils, pods, flowers, and seeds.

6. A bean plant regenerated from the tissue culture of claim 5, said plant having the morphological and physiological characteristics of bean cultivar H37113, wherein a representative sample of seed has been deposited under NCIMB No. 41703.

7. A method for producing a bean seed comprising crossing a first parent bean plant with a second parent bean plant and harvesting the resultant hybrid bean seed, wherein said first parent bean plant or second parent bean plant is the bean plant of claim 2.

8. A hybrid bean seed produced by the method of claim 7.

9. A method for producing an herbicide resistant bean plant comprising transforming the bean plant of claim 2 with a transgene that confers herbicide resistance to an herbicide selected from the group consisting of imidazolinone, sulfonylurea, glyphosate, glufosinate, L-phosphinothricin, triazine, and benzonitrile.

10. An herbicide resistant bean plant, or a part thereof, produced by the method of claim 9.

11. A method for producing an insect resistant bean plant comprising transforming the bean plant of claim 2 with a transgene that confers insect resistance.

12. An insect resistant bean plant, or a part thereof, produced by the method of claim 11.

13. A method for producing a disease resistant bean plant comprising transforming the bean plant of claim 2 with a transgene that confers disease resistance.

14. A disease resistant bean plant, or a part thereof, produced by the method of claim 13.

15. A method of introducing a desired trait into bean cultivar H37113 comprising:
   (a) crossing a bean cultivar H37113 plant grown from bean cultivar H37113 seed, wherein a representative sample of seed has been deposited under NCIMB No. 41703, with another bean plant that comprises a desired trait to produce $F_1$ progeny plants, wherein the desired trait is selected from the group consisting of insect resistance, disease resistance, water stress tolerance, heat tolerance, improved shelf life, and improved nutritional quality;
   (b) selecting one or more progeny plants that have the desired trait to produce selected progeny plants;
   (c) crossing the selected progeny plants with the bean cultivar H37113 plants to produce backcross progeny plants;
   (d) selecting for backcross progeny plants that have the desired trait and physiological and morphological characteristics of bean cultivar H37113 listed in Table 1 to produce selected backcross progeny plants; and
   (e) repeating steps (c) and (d) three or more times in succession to produce selected fourth or higher backcross progeny plants that comprise the desired trait and the physiological and morphological characteristics of bean cultivar H37113 listed in Table 1.

16. A bean plant produced by the method of claim 15, wherein the plant has the desired trait and the physiological and morphological characteristics of bean cultivar H37113 listed in Table 1.

17. A method for producing bean cultivar H37113 seed comprising crossing a first parent bean plant with a second parent bean plant and harvesting the resultant bean seed, wherein both said first and second bean plants are the bean plant of claim 4.

18. The bean plant of claim 16, wherein the desired trait is herbicide resistance and the resistance is conferred to an herbicide selected from the group consisting of imidazolinone, sulfonylurea, glyphosate, glufosinate, L-phosphinothricin, triazine, and benzonitrile.

19. The bean plant of claim 16, wherein the desired trait is insect resistance and the insect resistance is conferred by a transgene encoding a *Bacillus thuringiensis* endotoxin.

20. The bean plant of claim 16, wherein the desired trait is selected from the group consisting of insect resistance, disease resistance, water stress tolerance, heat tolerance, improved shelf life, and improved nutritional quality.

* * * * *